United States Patent
Ogura et al.

(10) Patent No.: US 9,968,315 B2
(45) Date of Patent: May 15, 2018

(54) ELECTRONIC CASSETTE AND ELECTRONIC CASSETTE SYSTEM

(71) Applicant: FUJIFILM Corporation, Tokyo (JP)

(72) Inventors: Ryosuke Ogura, Ashigarakami-gun (JP); Toshiyuki Nabeta, Ashigarakami-gun (JP); Jun Enomoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 114 days.

(21) Appl. No.: 14/838,530

(22) Filed: Aug. 28, 2015

(65) Prior Publication Data
US 2016/0081638 A1    Mar. 24, 2016

(30) Foreign Application Priority Data
Sep. 22, 2014   (JP) .................. 2014-193134

(51) Int. Cl.
    *A61B 6/00*   (2006.01)
(52) U.S. Cl.
    CPC .......... *A61B 6/4283* (2013.01); *A61B 6/4291* (2013.01); *A61B 6/4411* (2013.01)
(58) Field of Classification Search
    CPC .................................. A61B 6/4283
    See application file for complete search history.

(56) References Cited

U.S. PATENT DOCUMENTS

| | | | | |
|---|---|---|---|---|
| 8,172,461 B2* | 5/2012 | Liu | .............. | A61B 6/4283 378/114 |
| 8,492,717 B2* | 7/2013 | Ogura | ............ | A61B 6/4283 250/336.1 |
| 8,879,689 B2* | 11/2014 | Ohta | ............ | A61B 6/4233 378/108 |
| 9,134,436 B2* | 9/2015 | Kwak | ............ | A61B 6/548 |
| 9,535,176 B2* | 1/2017 | Miyoshi | ............ | G01T 7/00 |
| 2012/0217411 A1* | 8/2012 | Watanabe | ........ | A61B 6/4283 250/394 |
| 2013/0161526 A1* | 6/2013 | Tajima | ............ | A61B 6/5258 250/394 |

(Continued)

FOREIGN PATENT DOCUMENTS

| | | |
|---|---|---|
| JP | 3137548 U | 11/2007 |
| JP | 3144690 U | 9/2008 |

(Continued)

OTHER PUBLICATIONS

English Translation of WO2013015265.*

*Primary Examiner* — David J Makiya
*Assistant Examiner* — Soorena Kefayati
(74) *Attorney, Agent, or Firm* — Birch, Stewart, Kolasch & Birch, LLP (57) ABSTRACT

A housing of an electronic cassette includes an inclined surface. The inclined is formed between a side surface and a rear surface of the housing and inclined relative to the side surface and the rear surface. The inclined surface is provided with indicators for displaying a center position of each side of an imaging area and operation conditions of the electronic cassette. Each of the indicators consists of a light source and a display window through which light from the light source is emitted to the outside. The display window is formed on the inclined surface. Since the display window is formed on the inclined surface, the display window is not blocked by an outer grid.

13 Claims, 10 Drawing Sheets

(56) References Cited

U.S. PATENT DOCUMENTS

| | | | | |
|---|---|---|---|---|
| 2013/0301802 A1* | 11/2013 | Eguchi | ................... | H05G 1/08 378/98 |
| 2015/0131782 A1* | 5/2015 | Park | ................... | A61B 6/4283 378/62 |
| 2015/0366524 A1* | 12/2015 | Suzuki | ................. | A61B 6/4283 378/189 |

FOREIGN PATENT DOCUMENTS

| | | | |
|---|---|---|---|
| JP | WO2013015265 | * | 1/2013 |
| JP | 2013-33055 A | | 2/2013 |

* cited by examiner

ELECTRONIC CASSETTE AND ELECTRONIC CASSETTE SYSTEM

CROSS-REFERENCE TO RELATED APPLICATIONS

The present application claims priority under 35 U.S.C. § 119 to Japanese Patent Application No. 2014-193134, filed Sep. 22, 2014. The above application is hereby expressly incorporated by reference, in its entirety, into the present application.

BACKGROUND OF THE INVENTION

1. Field of the Invention

The present invention relates to an electronic cassette and an electronic cassette system for use in radiography.

2. Description Related to the Prior Art

An electronic cassette has been widely used in medical radiography, for example, in X-ray photography. An electronic cassette system includes an electronic cassette. The electronic cassette is a portable X-ray image detector provided with an built-in image detector (also referred to as flat panel detector (FPD)) for detecting an X-ray image of a subject such as a patient inside a housing having a front surface on which X-rays are incident, a rear surface facing the front surface, and four side surfaces.

The electronic cassette is set to be attachable to and detachable from a holder of an upright radiographic stand or a supine radiographic stand such that the electronic cassette is held in a posture in which an X-ray source for irradiating X-rays and the front surface of the housing face each other. Further, the electronic cassette is used alone for a subject lying on a bed or a subject who cannot move on his/her own such as an aged person or an emergency patient in some cases, in addition to being set to the holder of the upright radiographic stand or the supine radiographic stand.

Further, in X-ray photography, since scattered rays are generated upon transmission of X-rays through a subject, a grid for removing the scattered rays is used in some cases. There is a grid detachably attached to an electronic cassette externally (hereinafter referred to as external grid) (see Utility Model Registration No. 3137548 and Utility Model Registration No. 3144690). In the case where the electronic cassette is used alone, the outer grid is attached to the electronic cassette.

The external grid consists of a grid body and a holding frame for holding the grid body. The grid body is attached to the holding frame. The holding frame has a top panel for covering the front surface of the housing, and a side panel which is provided to an edge of the top panel and extends in a direction from a front-surface side to a rear-surface side of the housing so as to cover part of the side surface of the housing.

As shown in FIG. 1 of Japanese Patent Laid-Open Publication No. 2013-033055, an electronic cassette includes an indicator. The indicator functions to inform an operator such as a radiation technologist of operation conditions of the electronic cassette such as power on/off of the electronic cassette and whether or not preparation for detecting an X-ray image by an image detector has been completed, or a center position of each side of a rectangular imaging area of the image detector which serves as a mark in X-ray photography. The indicator includes a light source disposed inside a housing, and a display window disposed on an outer surface of the housing through which light from the light source is emitted to the outside. Utility Model Registration No. 3137548 discloses an LED (Light Emitting Diode) as a light source and a display window having a L-shape which is formed to extend from a side surface to a front surface of a housing.

However, in the case where the display window is formed on the side surface or the front surface of the housing as disclosed in Utility Model Registration No. 3137548, when the outer grid is attached to the electronic cassette, the display window is covered by the outer grid, and there arises a problem that it becomes impossible for an operator to check a display state of the indicator.

Further, even in the case where the outer grid is not attached to the electronic cassette, when the electronic cassette is inserted into a clearance between a subject and a mounting surface of a bed or the like on which the subject is lying, in particular, the display window formed on the front surface of the housing is covered by the subject, and there arises a problem that it becomes impossible for an operator to check a display state of the indicator.

SUMMARY OF THE INVENTION

In view of the foregoing, an object of the present invention is to provide an electronic cassette and an electronic cassette system in which a display state of an indicator can be checked even in the case where an outer grid is attached to the electronic cassette or other cases.

To achieve the above object of the present invention, an electronic cassette of the present invention includes an image detector, a housing for housing the image detector, and an indicator. The image detector detects a radiation image of a subject based on radiation having been transmitted through the subject. The housing has a front surface on which the radiation is incident, a rear surface facing the front surface, and four side surfaces. Additionally, the housing has an inclined surface which is formed at least between one of the side surfaces and the rear surface and inclined relative to the one of side surfaces and the rear surface. The indicator has a light source and a display window disposed at least on the inclined surface such that light is emitted from the light source to the outside through the display window.

Preferably, the image detector has a rectangular imaging area, and the indicator is disposed at a center position of one side of the imaging area. In this case, the display window preferably has an elongated shape in which a longitudinal direction of the display window extends in a direction perpendicular to the one side of the imaging area.

A mark is preferably formed on the side surface of the housing. The mark extends in a direction perpendicular to the one side of the imaging area from one end of the display window. The mark is preferably formed to extend from the side surface to the front surface of the housing.

The display window is preferably formed to extend from the inclined surface to the side surface. Preferably, the display window is formed to further extend from the side surface to the front surface.

The indicator preferably represents operation conditions. The operation conditions preferably include at least one of a ready state indicating that preparation for detecting the radiation image by the image detector has been completed, an error state indicating an abnormal operation, and a selected state indicating that selection of an electronic cassette to be used in radiography has been completed.

Preferably, the light source is configured to emit light having plural different colors and emit light having a color preliminarily registered from among the plural colors in the selected state.

The display window preferably consists of an opening and a cover having light permeability. The cover blocks the opening.

It is preferable that an outer grid for removing scattered rays generated upon transmission of the radiation through the subject is detachably attached. Preferably, the outer grid includes a top panel for covering the front surface of the housing, and a side panel provided to an edge of the top panel. The side panel extends in a direction from the front surface to the rear surface of the housing, so as to cover part of the side surface of the housing.

An electronic cassette system of the present invention includes an electronic cassette and an outer grid detachably attached to the electronic cassette. The electronic cassette includes an image detector, a housing for housing the image detector, and an indicator. The image detector detects a radiation image of a subject based on radiation having been transmitted through the subject. The housing has a front surface on which the radiation is incident, a rear surface facing the front surface, and four side surfaces. Additionally, the housing has an inclined surface which is formed at least between one of the side surfaces and the rear surface and inclined relative to the one of the side surfaces and the rear surface. The indicator has a light source and a display window disposed at least on the inclined surface such that light is emitted from the light source to the outside through the display window. The outer grid removes scattered rays generated upon transmission of the radiation through the subject.

Preferably, the outer grid includes a top panel for covering the front surface of the housing, and a side panel provided to an edge of the top panel. The side panel extends in a direction from the front surface to the rear surface of the housing, so as to cover part of the side surface of the housing.

According to the present invention, since the display window through which the light from the light source is emitted to the outside is formed on the inclined surface which is inclined relative to the side surface and the rear surface of the housing, the display window is not blocked by the outer grid and the like. Consequently, it is possible to provide the electronic cassette and the electronic cassette system in which the display state of the indicator can be checked even in the case where the outer grid is attached to the electronic cassette or other cases.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
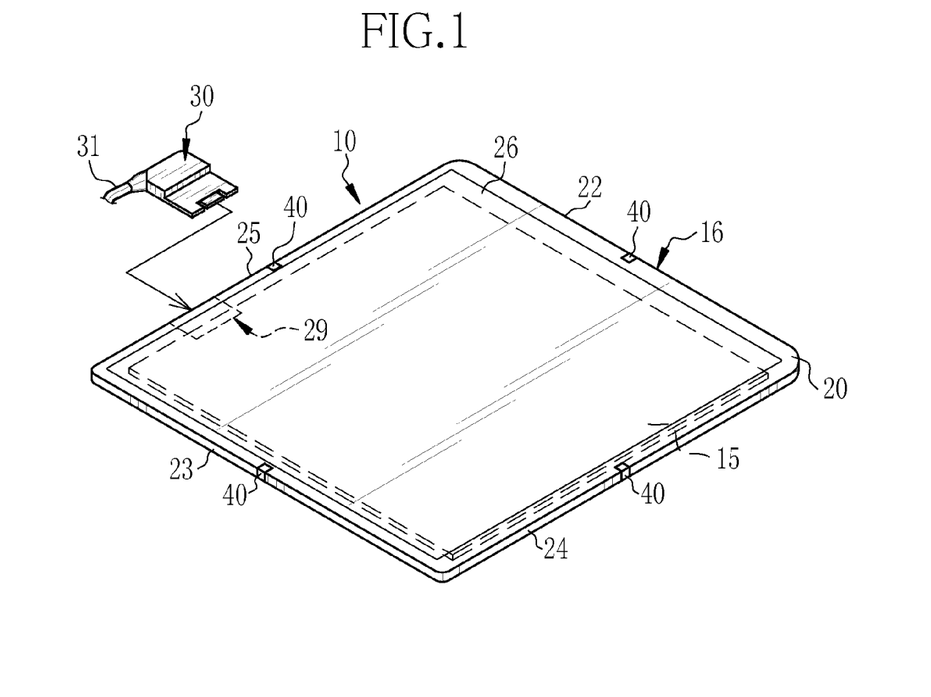
FIG. 1 is a perspective view illustrating an external appearance of an electronic cassette as viewed from a front side thereof.
Figure 2:
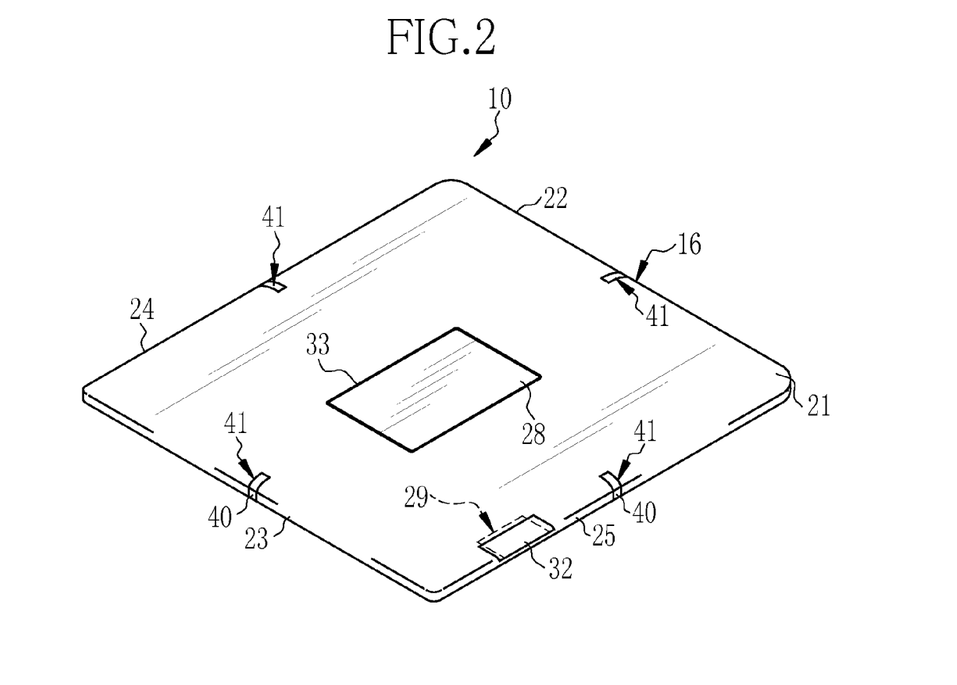
FIG. 2 is a perspective view illustrating an external appearance of the electronic cassette as viewed from a rear side thereof.

In FIGS. 1 and 2, an electronic cassette 10 is used for medical radiography, for example, and consists of an image detector 15 and a portable housing 16 for housing the image detector 15. The image detector 15 detects an X-ray image of a subject based on X-rays having been transmitted through the subject.

As well known, the image detector 15 includes a scintillator (phosphor) for converting incident X-rays into visible light beams, and a thin film transistor (TFT) active matrix substrate. A rectangular imaging area 45 (see FIG. 3) is formed on the TFT active matrix substrate. A plurality of pixels each of which accumulates charge corresponding to the visible light beams from the scintillator are arranged on the imaging area 45. The housing 16 incorporates not only the image detector 15 but also a gate driver, a signal processing circuit, a control section, and the like. The gate driver supplies a gate pulse to a gate of the TFT to switch the TFT. The signal processing circuit converts the charge accumulated in each of the pixels into a voltage signal representing an X-ray image and outputs the voltage signal. The control section controls operation of each of the gate driver and the signal processing circuit.

The housing 16 consists of a front surface 20 on which the X-rays are incident, a rear surface 21 facing the front surface 20, and four side surfaces 22, 23, 24, and 25, so as to have a rectangular parallelepiped shape. The housing 16 is made of electrically-conductive resin, for example. The housing 16 also functions as an electromagnetic shield for preventing electromagnetic noise from entering the electronic cassette 10 and preventing electromagnetic noise from being emitted from the electronic cassette 10 to the outside. The housing 16 has a size compliant with the ISO (International Organization for Standardization) 4090: 2001 which is substantially the same as the size of each of a film cassette, an IP (Imaging Plate) cassette, and a CR (Computed Radiography) cassette, for example.

The electronic cassette 10 is set to be attachable to and detachable from a holder of an upright radiographic stand or a supine radiographic stand, such that the electronic cassette 10 is held in a posture in which an X-ray source for irradiating X-rays and the front surface 20 of the housing 16 face each other. Further, the electronic cassette 10 is used alone for a subject lying on a bed or a subject who cannot move on his/her own such as an aged person or an emergency patient in some cases, in addition to being set to the holder of the upright radiographic stand or the supine radiographic stand. Furthermore, in the case where the housing 16 has substantially the same size as that of the film cassette, the IP cassette, and the CR cassette, the electronic cassette 10 can be attached to an existing radiographic stand for these cassettes.

A rectangular opening is formed on the front surface 20 of the housing 16. A transmission plate 26 is attached to the opening. A protection film 27 (see FIG. 5) made of a resin, through which the X-rays are transmitted, is adhered to a surface of the transmission plate 26. This allows the front surface 20 to be a flat surface. The transmission plate 26 has a plane size slightly larger than that of the imaging area 45 (see FIG. 3). The transmission plate 26 is made of a carbon material which is lightweight, highly rigid, and extremely permeable to the X-rays.

The electronic cassette 10 includes a control device 100 (see FIG. 10) for controlling the operation of the electronic cassette 10, an antenna for generating a radio wave for wireless communication of various kinds of information such as X-ray images, and an oscillation circuit (not shown). In the case where such a wireless communication function is used, the electronic cassette 10 is activated by the electricity from a battery 28, namely, the electronic cassette 10 can be used without a cable.

Further, the electronic cassette 10 includes a female connector 29 which functions for wired communication with the control device 100. A male connector 30 is connected to the female connector 29. One end of a cable 31 for connecting the electronic cassette 10 to the control device 100 in a wired manner is connected to the male connector 30. The other end of the cable 31 is connected to a connector (not shown) connected to the control device 100. During the use of the wireless communication function, the female connector 29, to which the male connector 30 is not connected, is covered and protected by a lid 32.

The electronic cassette 10 receives not only the various kinds of information but also electricity through the female connector 29 from the control device 100. In the case where the female connector 29 and the male connector 30 are connected to each other, the electronic cassette 10 is activated by the electricity from the control device 100. It is also possible to charge the battery 28 with use of the electricity from the control device 100.

A battery mounting section 33 is formed at the center of the rear surface 21. The battery 28 for supplying electricity to activate the electronic cassette 10 is detachably mounted on the battery mounting section 33. FIG. 2 shows a state that the battery 28 is mounted on the battery mounting section 33.

The battery mounting section 33 is a concave portion in which the rear surface 21 is recessed toward the front surface 20. The battery mounting section 33 is formed to have the same planar shape and the same planar size as those of the battery 28 such that the battery 28 is fit into the battery mounting section 33 substantially without a gap. Additionally, the depth of the battery mounting section 33 from the rear surface 21 is substantially the same as the thickness of the battery 28. Therefore, in the state that the battery 28 is mounted on the battery mounting section 33 as shown in FIG. 2, an upper surface of the battery 28 is exposed through the rear surface 21, and the upper surface of the battery 28 and the rear surface 21 are on the same plane.

Figure 3:
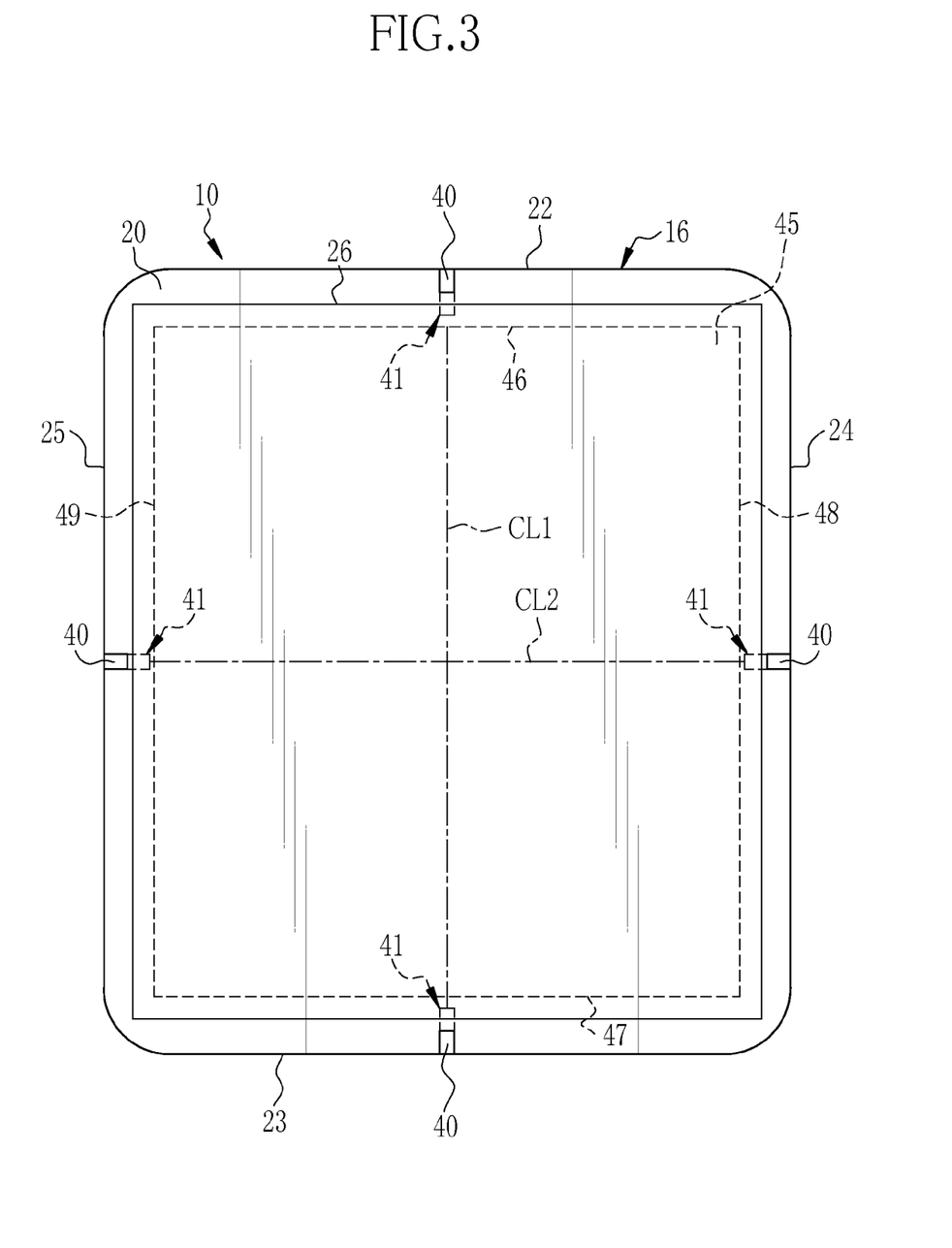
FIG. 3 is a view illustrating positions at which indicators and marks are disposed.

Four marks 40 and four indicators 41 are formed on the electronic cassette 10. As shown in FIG. 3, the marks 40 and the indicators 41 are formed one by one at a center position of each of four sides 46, 47, 48, and 49 of the imaging area 45. More specifically, the marks 40 and the indicators 41 are respectively formed one by one on an extended line of a line CL1 and an extended line of a line CL2 each shown by a dashed-dotted line in FIG. 3. The line CL1 connects the center position of the side 46 and the center position of the side 47 facing each other in the imaging area 45. The line CL2 connects the center position of the side 48 and the center position of the side 49 facing each other in the imaging area 45. Namely, the marks 40 and the indicators 41 function to inform an operator of the center position of each of the sides 46, 47, 48, and 49 of the imaging area 45. A line representing CL1 and a line representing CL2 are formed on the transmission plate 26 by printing or the like so as to show the center position of each of the sides 46, 47, 48, and 49 of the imaging area 45 together with the marks 40 and the indicators 41. Incidentally, the line representing CL1 and the line representing CL2 are not shown in the drawing, since they are respectively overlapped with the CL1 and CL2.

The indicators 41 inform the operator not only the center position of each of the sides 46 to 49 of the imaging area 45 but also the operation conditions of the electronic cassette 10. As the operation conditions of the electronic cassette 10, there are a power on/off state of the electronic cassette 10, a ready state indicating that preparation for detecting an X-ray image by the image detector 15 has been completed, an error state indicating an abnormal operation of the electronic cassette 10, a selected state indicating that the electronic cassette 10 concerned has been selected to be used in X-ray photography, and the like. Incidentally, although the positions at which the four marks 40 are formed are different from one another, the configuration and operation of them is the same. Similarly, although the positions at which the four indicators 41 are formed are different from one another, the configuration and operation of them is the same. Therefore, only the mark 40 and the indicator 41 formed at the side of the side surface 22 are explained hereinbelow. Note that, the indicator 41 is not necessarily formed at the center position of each of the sides 46 to 49 of the imaging area 45. The indicator 41 may be formed at a position other than the center position of each of the sides 46 to 49 of the imaging area 45, and may function only to inform the operator of the operation conditions of the electronic cassette 10 described above.

Figure 4:
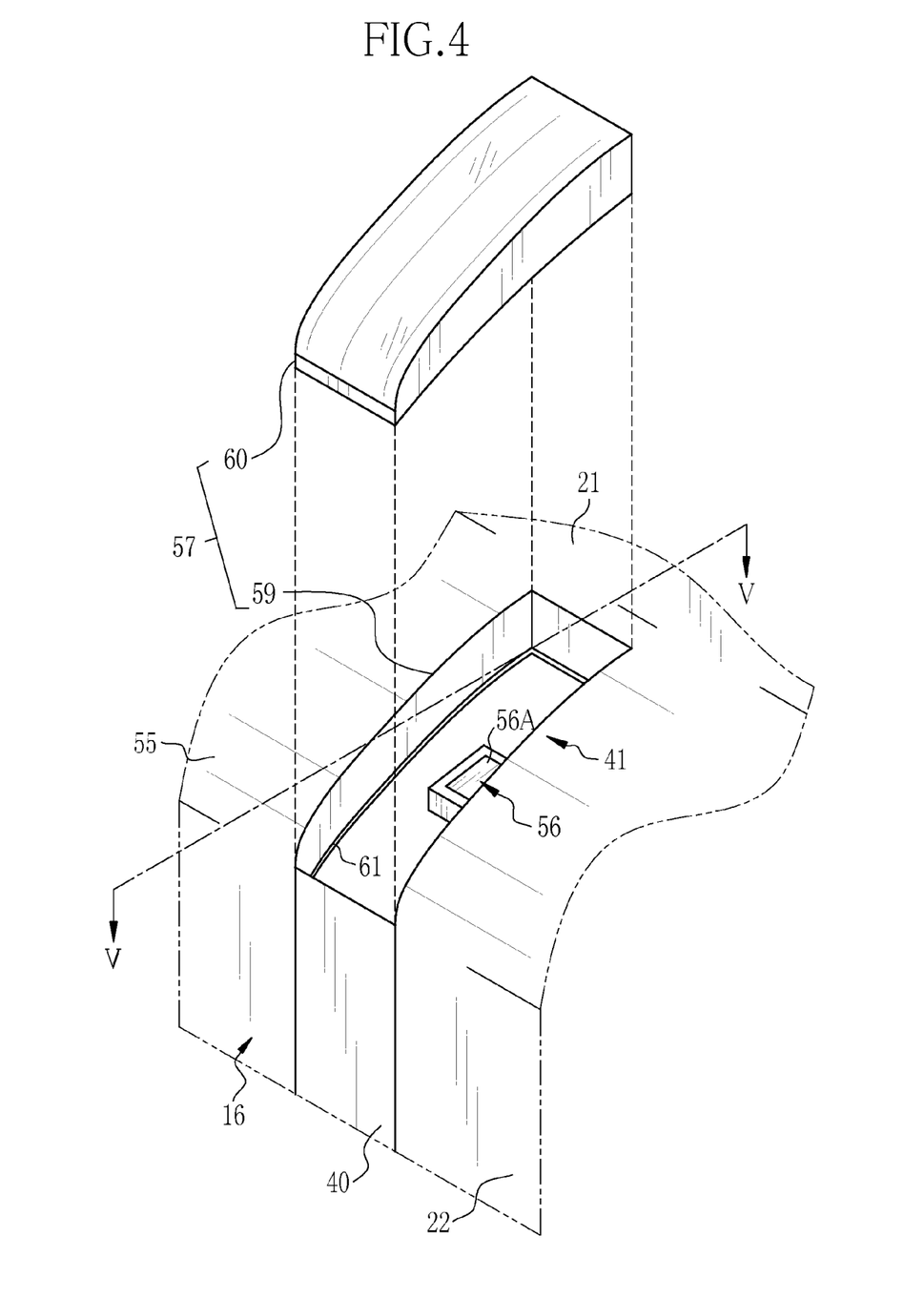
FIG. 4 is a perspective view illustrating an external appearance of the indicator and its periphery.
Figure 5:
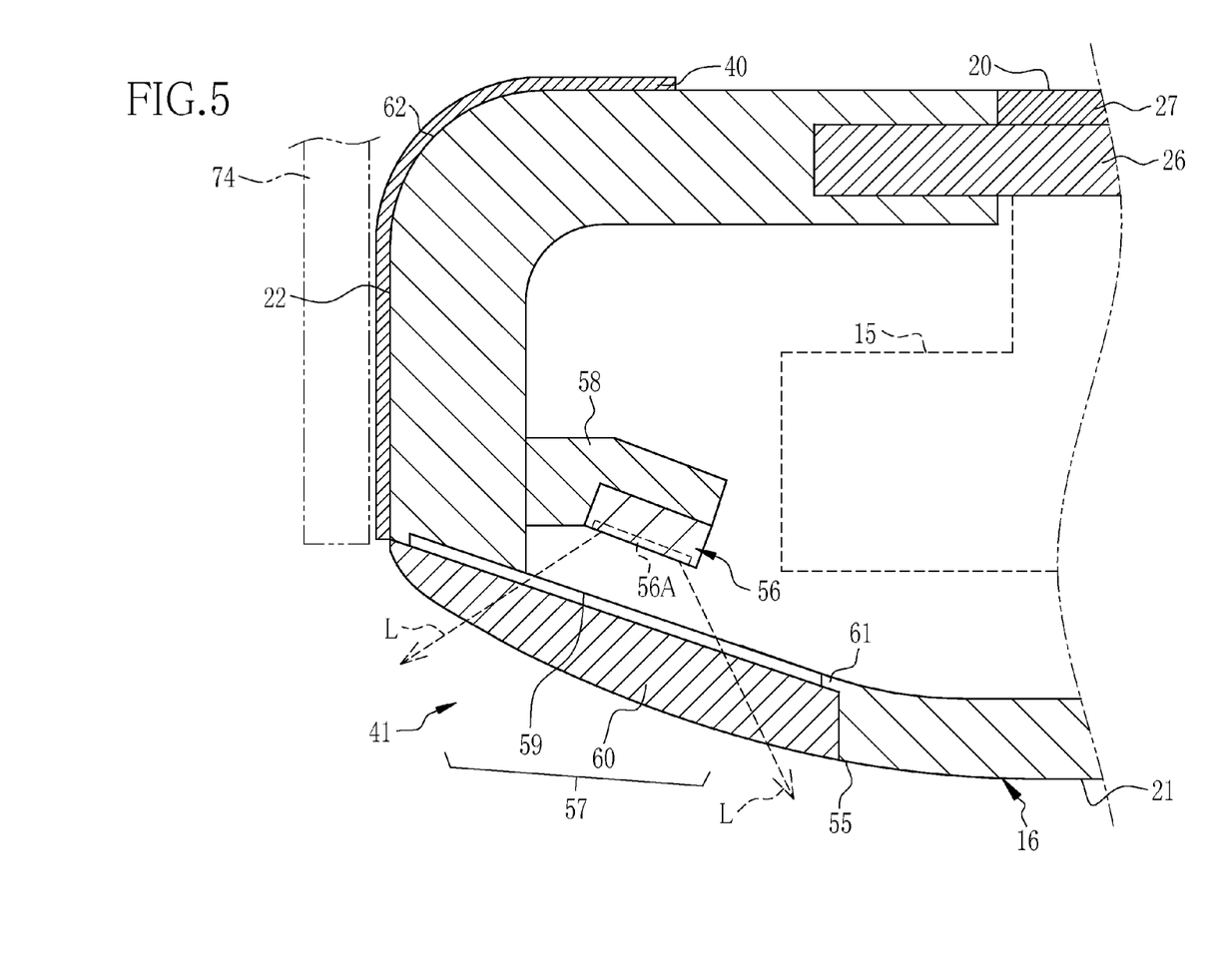
FIG. 5 is a cross-sectional view of a housing taken along a line V-V of FIG. 4.

FIG. 4 illustrates the indicator 41 and its periphery, and FIG. 5 is a cross-sectional view of the housing 16 taken along a line V-V of FIG. 4. In FIGS. 4 and 5, an inclined surface 55, which is inclined relative to the side surface 22 and the rear surface 21 of the housing 16, is formed between the side surface 22 and the rear surface 21. The indicator 41 is formed on the inclined surface 55.

The indicator 41 includes a light source 56 disposed inside the housing 16 and a display window 57 formed on the inclined surface 55. As the light source 56, a light-emitting element such as an LED or an organic EL (Electro-Luminescence) is used, for example. The light source 56 is attached to an attachment section 58 formed to protrude from an inner surface of the housing 16. The light source 56 is located at substantially the center of the display window 57, such that a light emitting section 56A faces the inclined surface 55. The light source 56 emits light L toward the display window 57. The light L from the light source 56 is emitted through the display window 57 to the outside of the housing 16.

The light source 56 can emit the light L of plural different colors. The light source 56 changes the color of the light L in accordance with the operation conditions of the electronic cassette 10. For example, the light source 56 represents the power-on state of the electronic cassette 10 by emitting green light L, the ready state by emitting blue light L, the error state by emitting red light L, and the selected state by emitting orange light L (see FIG. 10).

The display window 57 has an elongated shape. Specifically, a width of the display window 57 along a direction parallel to the side 46 of the imaging area 45 is shorter than a length of the display window 57 along a direction perpendicular to the side 46 of the imaging area 45. Namely, a longitudinal direction of the display window 57 extends in the direction perpendicular to the side 46 on the inclined surface 55. The display window 57 consists of an opening 59 formed on the inclined surface 55 and a cover 60 for blocking the opening 59. The cover 60 has light permeability and light diffusion properties. The light L emitted from the light source 56 is transmitted through the cover 60 and diffused inside the cover 60. Thereby, the light L is diffused over an entire upper surface of the cover 60, and emitted as diffused light to the outside of the housing 16.

An edge 61 for receiving the cover 60 is formed on an inner periphery of the opening 59. The edge 61 regulates a position to which the cover 60 is attached in an insertion direction of the cover 60 into the opening 59.

The cover 60 has the same shape and the same size as those of the opening 59, and is fit into the opening 59 substantially without a gap. In a state that the cover 60 is fit into the opening 59 as shown in FIG. 5, the upper surface of the cover 60 and the inclined surface 55 are on the same plane. The cover 60 and the opening 59 are fixed to each other by an adhesive, for example. The opening 59 is blocked by the cover 60 in a water-tight manner and in an air-tight manner.

The mark 40 extends in the direction perpendicular to the side 46 of the imaging area 45 from one end of the display window 57 on the side surface 22. The mark 40 also extends to the front surface 20. The width of the mark 40 in a direction parallel to the side 46 is the same as the width of the display window 57. The mark 40 is formed by printing, painting, or adhesion of a sticker, for example.

The reference numeral 62 denotes an inclined surface formed between the side surface 22 and the front surface 20 of the housing 16 in the similar manner as the inclined surface 55. Each of the inclined surfaces 55 and 62 is a curved surface which is convex toward the outside of the housing 16. Incidentally, although not shown in the drawing, the inclined surface 55 is also formed between the rear surface 21 and the side surfaces 23 to 25, respectively, and the inclined surface 62 is also formed between the front surface 20 and the side surfaces 23 to 25, respectively, in the similar manner as the side surface 22.

Figure 6:
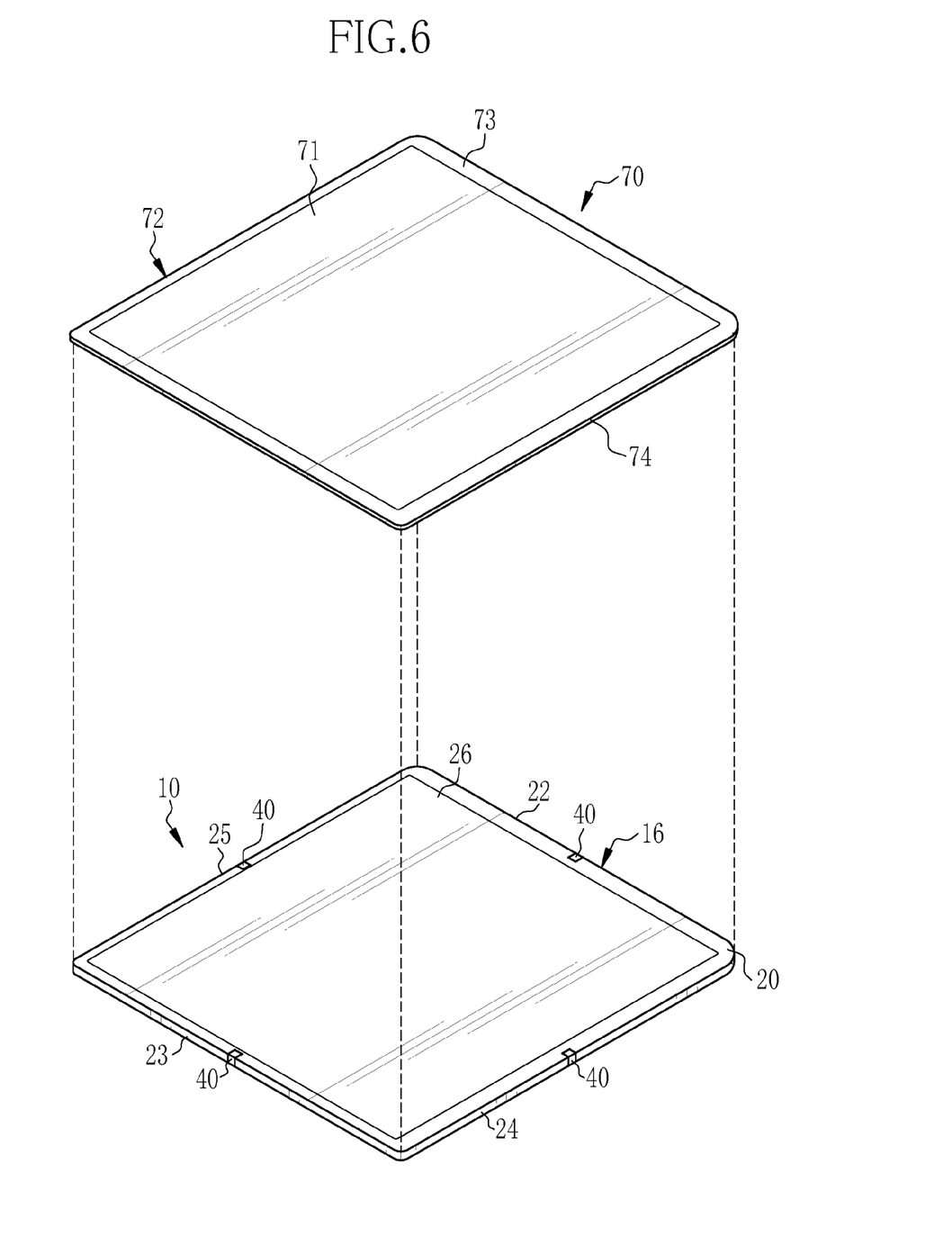
FIG. 6 is a perspective view illustrating an external appearance of each of an outer grid and the electronic cassette.

In X-ray photography, since scattered rays are generated upon transmission of X-rays through a subject, an outer grid 70 shown in FIG. 6 is used for the purpose of removing the scattered rays in the case where the electronic cassette 10 is used alone, in some cases. The outer grid 70 is detachably attached to the housing 16 externally. The outer grid 70 consists of a rectangular grid body 71 and a holding frame 72 for holding the grid body 71. The grid body 71 is slightly larger than the transmission plate 26 so as to cover the entire transmission plate 26 when the outer grid 70 is attached to the housing 16. Further, the holding frame 72 is slightly larger than the housing 16.

The holding frame 72 has a top panel 73 and a side panel 74. The top panel 73 has a rectangular opening to which the grid body 71 is attached. When the outer grid 70 is attached to the housing 16, the top panel 73 and the grid body 71 cover the front surface 20 of the housing 16. The side panel 74 is provided to an edge of the top panel 73, and extends in a direction from the front surface 20 to the rear surface 21. Incidentally, although not shown in the drawing, the holding frame 72 is provided with a well-known dropping prevention/dropping prevention releasing mechanism. The dropping prevention/dropping prevention releasing mechanism fixes the outer grid 70 to the housing 16 so as to prevent the outer grid 70 from being dropped, and releases the dropping prevention.

In order to facilitate the positioning of the outer grid 70 relative to the housing 16, the side panel 74 has a length enough to reach a border between the side surface 22 and the inclined surface 55 as shown by a chain double-dashed line in FIG. 5, for example. Accordingly, when the outer grid 70 is attached to the housing 16, the side surface 22 is covered by the side panel 74. Incidentally, the outer grid 70 and the electronic cassette 10 constitute the electronic cassette system of the present invention.

Figure 7:
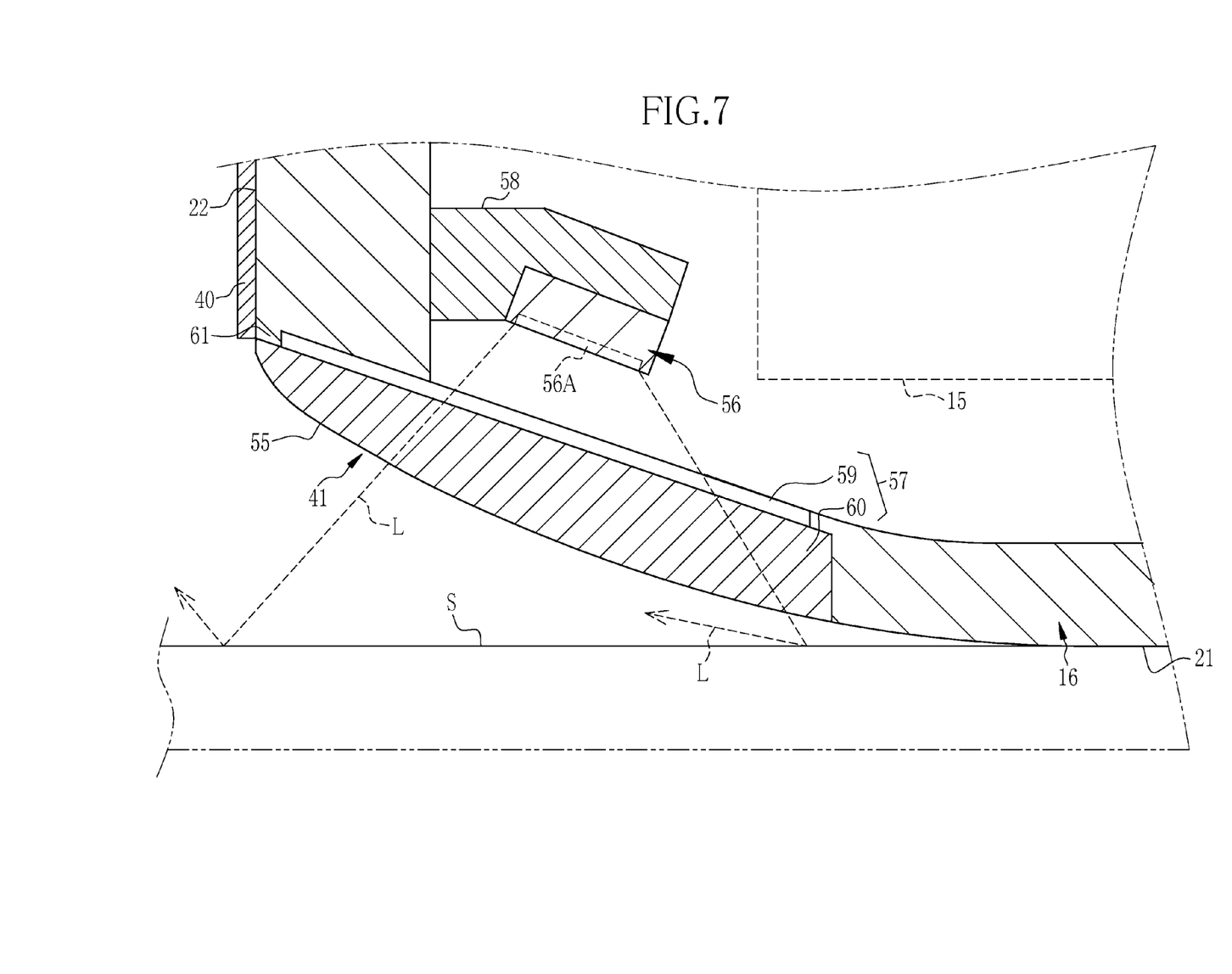
FIG. 7 is a view illustrating a display state of the indicator in the case where the electronic cassette is mounted on a flat mounting surface.

Next, an operation of the above configuration is explained. At first, in the case where the electronic cassette 10 is used alone for a subject lying on a bed or a subject who cannot move on his/her own such as an aged person or an emergency patient, the electronic cassette 10 is installed on a flat installation surface S such as a bed or a floor surface with the rear surface 21 facing downward, as shown in FIG. 7. In this case, although the rear surface 21 is blocked by the installation surface S, a gap is secured between the inclined surface 55 and the installation surface S. Accordingly, the light L emitted through the display window 57 formed on the inclined surface 55 illuminates the installation surface S just below the display window 57. An operator can perceive the center position of each of the sides 46 to 49 of the imaging area 45 and the operation conditions of the electronic cassette 10 by the light L which is applied to the installation surface S and reflected on the installation surface S, i.e., indirect light L.

Since the indicator 41 is formed at the center position of each of the sides 46 to 49 of the imaging area 45, the positioning between an X-ray irradiation field and the imaging area 45 and the positioning between the imaging area 45 and the subject are facilitated.

Further, in the case where the electronic cassette 10 is used alone, the outer grid 70 is attached to the housing 16 in order to remove the scattered rays generated upon transmission of X-rays through the subject.

Figure 8:
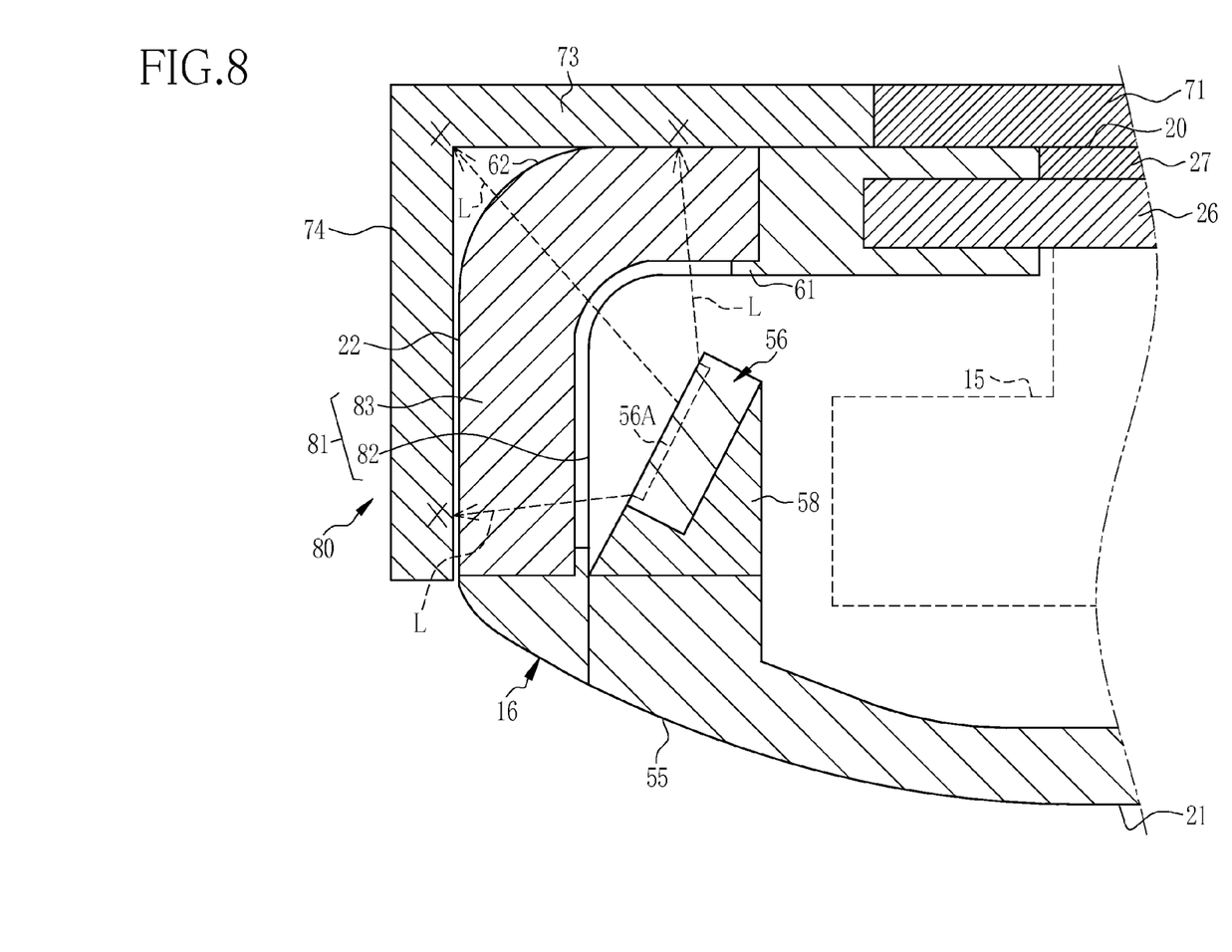
FIG. 8 is a view illustrating a comparative example in which a display window is formed to extend from a side surface to a rear surface of the housing.

In a comparative example shown in FIG. 8, a display window 81 of an indicator 80 is not formed on the inclined surface 55. Alternatively, the display window 81 is formed to extend from the side surface 22 to the front surface 20. In the similar manner as the display window 57, the display window 81 consists of an opening 82 formed to extend from the side surface 22 to the front surface 20, and a cover 83 for blocking the opening 82. The cover 83 has light permeability and light diffusion properties. The light source 56 is disposed at a position where the light emitting section 56A faces the side surface 22 and the inclined surface 62. Incidentally, in this case, the mark 40 is not formed.

In this case, when the outer grid 70 provided with the side panel 74 having the length enough to reach the border between the side surface 22 and the inclined surface 55 as shown by a chain double-dashed line in FIG. 5 is attached to the housing 16, the side surface 22 is blocked by the side panel 74. Additionally, the inclined surface 62 and the front surface 20 are also blocked by the side panel 74 and the top panel 73. Consequently, the light L from the light source 56 is intercepted by the outer grid 70 and is not emitted to the outside. Therefore, the operator cannot check the display state of the indicator 41.

However, according to this embodiment, since the display window 57 is formed on not the side surface 22 and the front surface 20 but the inclined surface 55, the display window 57 is not blocked by the outer grid 70, as shown in FIG. 5. Accordingly, even in the case where the outer grid 70 is attached to the electronic cassette 10, it is possible to check the display state of the indicator 41. Incidentally, since the display window 57 is formed on the inclined surface 55 as with this embodiment, even when the side panel 74 of the outer grid 70 has a length enough to exceed the border between the side surface 22 and the inclined surface 55, a small gap between the side panel 74 and the installation surface S allows the light L reflected on the installation surface S to pass through the gap. Thus, it is possible to check the display state of the indicator 41.

In the case where the display window 81 is formed to extend from the side surface 22 to the front surface 20 and the outer grid 70 is not used as with the comparative example shown in FIG. 8, the operator and the subject feel the light L directly entering eyes of them bright in some cases, in comparison with the case where the display window 57 is formed on the inclined surface 55 so as to show the display state of the indicator 41 by the light L which is reflected on the installation surface S, i.e., indirect light L as with this embodiment. Further, the display state of the indicator 41 is necessary information for the operator, but unnecessary information for the subject. Therefore, if the light L directly enters the eyes of the subject through the display window 81, the subject may feel irritated or anxious with the light L, because the subject does not know what the display state of the indicator 41 means.

Consequently, the display window 57 is formed on the inclined surface 55 such that the indirect light L reflected on the installation surface S shows the display state of the indicator 41 in this embodiment. Therefore, the operator and the subject do not feel the light L bright, and do not feel irritated or anxious with the light L. Further, instead of providing the display window 57 of the comparative example shown in FIG. 8, the mark 40 is formed to extend from the side surface 22 to the front surface 20 of the housing 16. Accordingly, in the case where the outer grid 70 is not used in X-ray photography, the operator can perceive the center position of each of the sides 46 to 49 of the imaging area 45 by not only the indicator 41 but also the mark 40.

Since the display window 57 has the elongated shape such that the longitudinal direction of thereof extends in the direction perpendicular to the side 46, and the width of the mark 40 in the direction parallel to the side 46 is the same as the width of the display window 57, it is possible to perceive the center position of each of the sides 46 to 49 of the imaging area 45a in a pinpointed manner. Thus, the center position of each of the sides 46 to 49 of the imaging area 45 can be readily identified.

Further, in the case where the opening 82 of the display window 81 is formed to extend from the side surface 22 to the front surface 20 of the housing 16 as in the case of the comparative example shown in FIG. 8, the strength of each of the side surface 22 and the front surface 20 is lower in comparison with the case where the opening 82 is not formed. In the case where the electronic cassette 10 is inserted into the clearance between the subject lying on the bed and the bed to perform X-ray photography, a load of the subject is intensively applied to the side surface 22 and the front surface 20, in particular, to the side surface 22, and therefore the low strength of the side surface 22 and the front surface 20 causes uneasiness. In contrast, in the case where the strength of the side surface 22 is secured, even if the strength of the inclined surface 55 becomes lower due to the opening 59 formed on the inclined surface 55, it is possible to perform X-ray photography without constraint.

Furthermore, in the case where the strength of the side surface 22 of the housing 16 is secured, even if the electronic cassette 10 is dropped by mistake, the electronic cassette 10 is hardly damaged. The main reason why the dropped electronic cassette 10 is damaged is that the side surface 22 or the corner of the housing 16 is hit against the ground and the side surface 22 is applied with an impact. Accordingly, in the case where the strength of the side surface 22 is secured, it is possible to prevent the electronic cassette 10 from being damaged at the time of being dropped.

The opening 59 is blocked by the cover 60. This allows the inclined surface 55 to be a flat surface. Thus, when the electronic cassette 10 is inserted into the clearance between the subject lying on the bed and the bed, the opening 59 is not caught on the bed, and does not interfere with the operation.

The provision of the inclined surfaces 55 and 62 allows the front surface 20, the rear surface 21, and the side surfaces 22 to 25 to be connected to each other by a smoothly curved surface having no corner. Therefore, the sense of touch with the housing 16 for the subject becomes softer. Further, in the case where the electronic cassette 10 is placed on the flat installation surface S, it is possible to lift up the electronic cassette 10 easily by putting a finger on the inclined surfaces 55 and 62. Additionally, it is possible to smoothly insert the electronic cassette 10 into the clearance between the subject lying on the bed and the bed.

Note that, although both the center position of each of the sides 46 to 49 of the imaging area 45 and the operation conditions of the electronic cassette 10 are displayed by the same indicator 41 in the first embodiment, an indicator for representing the center position of each of the sides 46 to 49 of the imaging area 45 and an indicator for displaying the operation conditions of the electronic cassette 10 may be separately disposed.

Although the mark 40 extends from the side surface 22 to the front surface 20 in the first embodiment, it is sufficient that the mark 40 is formed at least on the side surface 22.

Figure 9:
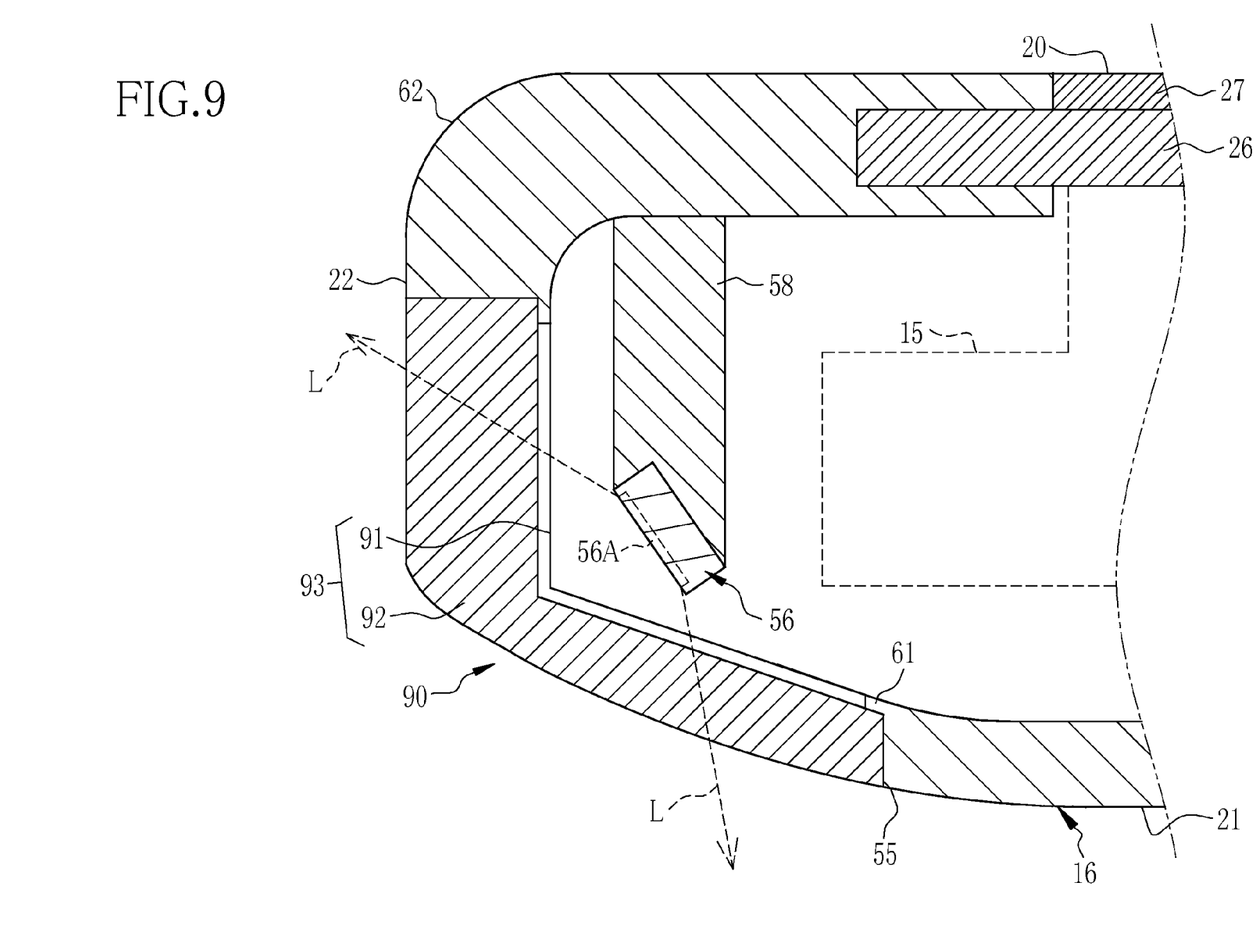
FIG. 9 is a view illustrating an example in which the display window is formed to extend from an inclined surface to the side surface of the housing.

Incidentally, as in the case of an indicator 90 shown in FIG. 9, a display window 93 consisting of an opening 91 and a cover 92 may be formed to extend from the inclined surface 55 to the side surface 22. In the case where the outer grid 70 is not used in X-ray photography, it is possible to check the display state of the indicator 90 by the light L emitted through the display window 93 formed to extend to the side surface 22. Further, although not shown in the drawing, the display window 93 may be formed to further extend from the side surface 22 to the front surface 20.

The shape of the display window is not limited to the elongated shape as in the case of the first embodiment. The length of the display window in the direction perpendicular to the side 46 of the imaging area 45 may be the same as the width of the display window in the direction parallel to the side 46 of the imaging area 45 on the inclined surface 55. Alternatively, the width of the display window in the direction parallel to the side 46 of the imaging area 45 may be larger than the length of the display window in the direction perpendicular to the side 46 of the imaging area 45. Additionally, the display window is not necessarily rectangular, and may be circle or oval.

Although the inclined surface 55 is formed between the rear surface 21 and each of the four side surfaces 22 to 25 and the four indicators 41 are disposed one-by-one on the inclined surfaces 55 respectively in the first embodiment, it is sufficient that only one indicator 41 is provided, and it is sufficient that the inclined surface 55 is formed at least between the rear surface 21 and the side surface provided with the indicator 41.

Second Embodiment

In a radiography room of a medical facility, a plurality of the electronic cassettes 10 are installed and controlled by one control device in many cases. In the case where a plurality of the electronic cassettes 10 are installed in the radiography room as described above, if the light L having the same color is emitted from the light sources 56 of a plurality of the electronic cassettes 10 at the time of displaying the selected state for indicating that the electronic cassette 10 for use in X-ray photography has been selected by the indicator 41, it is difficult for the operator to tell whether or not the electronic cassette 10 which displays the selected state by the indicator 41 is identical with the electronic cassette 10 actually required to be used by the operator.

Consequently, according to this embodiment, the color of the light L to be emitted from the light source 56 is preliminarily registered in each of a plurality of the electronic cassettes 10, such that the light L having the preliminarily registered color is emitted from each of the light sources 56 at the time of displaying the selected state.

Figure 10:
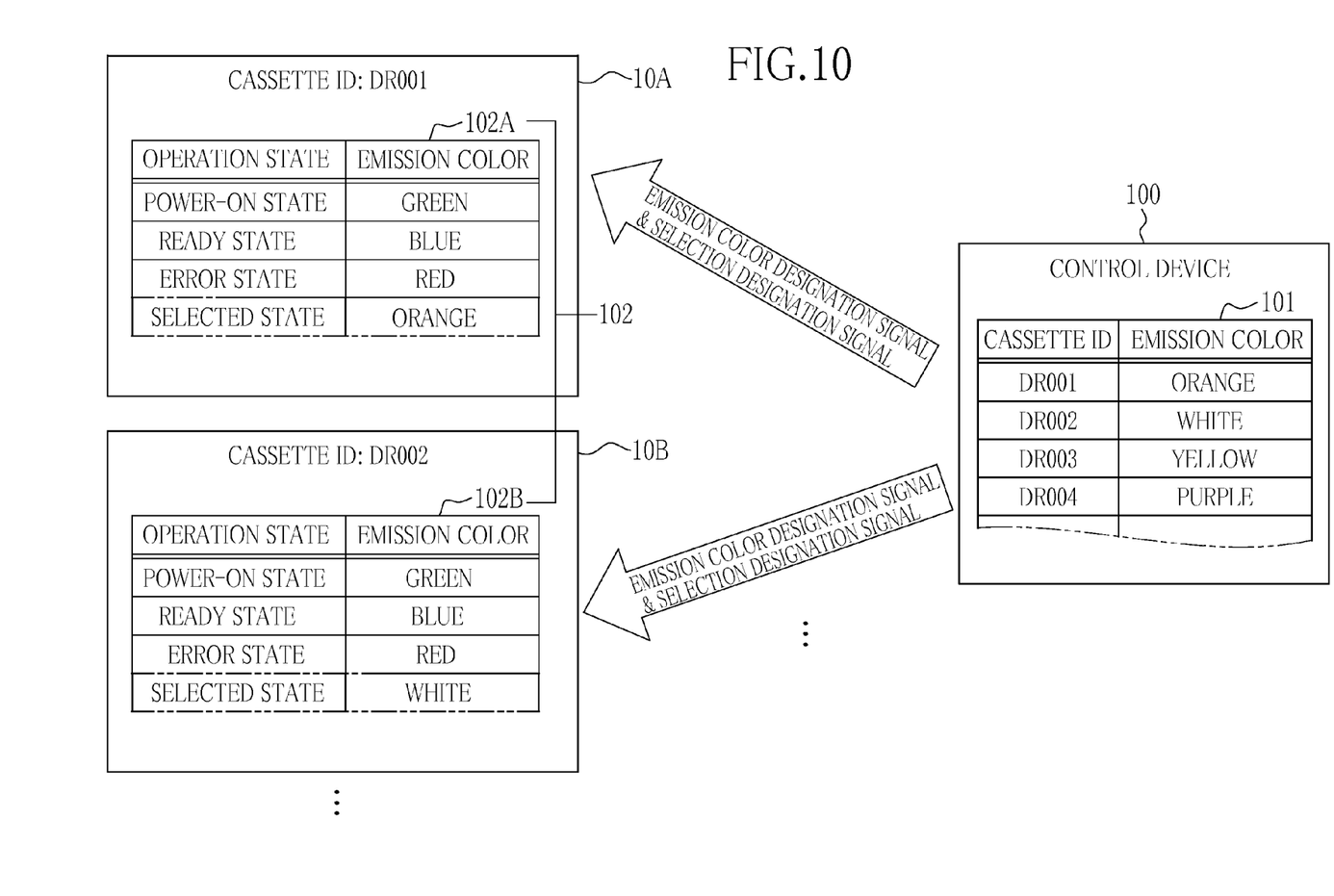
FIG. 10 is a view illustrating a second embodiment in which light having a color preliminarily registered, from among light having plural different colors, is emitted from a light source when the electronic cassette is in a selected state.

Specifically, as shown in FIG. 10, a cassette-emission color list 101 is preliminarily stored in a hard disk or the like of the control device 100. The cassette-emission color list 101 shows an emission color for each of a plurality of electronic cassettes 10A, 10B, . . . in the selected state. A cassette ID (Identification Data) as the number for identifying each of the electronic cassettes 10 and the emission color of the light L corresponding to each cassette ID are registered in the cassette-emission color list 101. For example, "orange" is registered as the emission color in the electronic cassette 10A having the cassette ID "DR001".

The cassette ID and the emission color in the cassette-emission color list 101 is manually inputted by an operator using a display screen and an input device such as a keyboard and a mouse of the control device 100 at the time of newly introducing the electronic cassettes 10, for example. The control device 100 transmits an emission color designation signal indicative of the inputted emission color to the electronic cassettes 10 concerned.

In contrast, operation condition-emission color lists 102A, 102B, . . . are stored in a ROM (Read Only Memory) or the like of each the electronic cassettes 10A, 10B, . . . . An emission color for each of the operation conditions such as the power-on state and the ready state of the electronic cassette 10 is registered in each of the operation condition-emission color lists 102A, 102B, . . . . The emission colors representing the operation conditions except the selected state shown by a chain double-dashed line in FIG. 10 in the operation condition-emission color lists 102A, 102B, . . . are preliminarily registered by a manufacturer before shipping of the electronic cassettes 10, for example. Incidentally, the emission colors of the operation conditions except the selected state are unified among a plurality of the electronic cassettes 10A, 10B, . . . . In contrast, the emission color representing the selected state is rewritten in accordance with the emission color designation signal from the control device 100.

Figure 11:
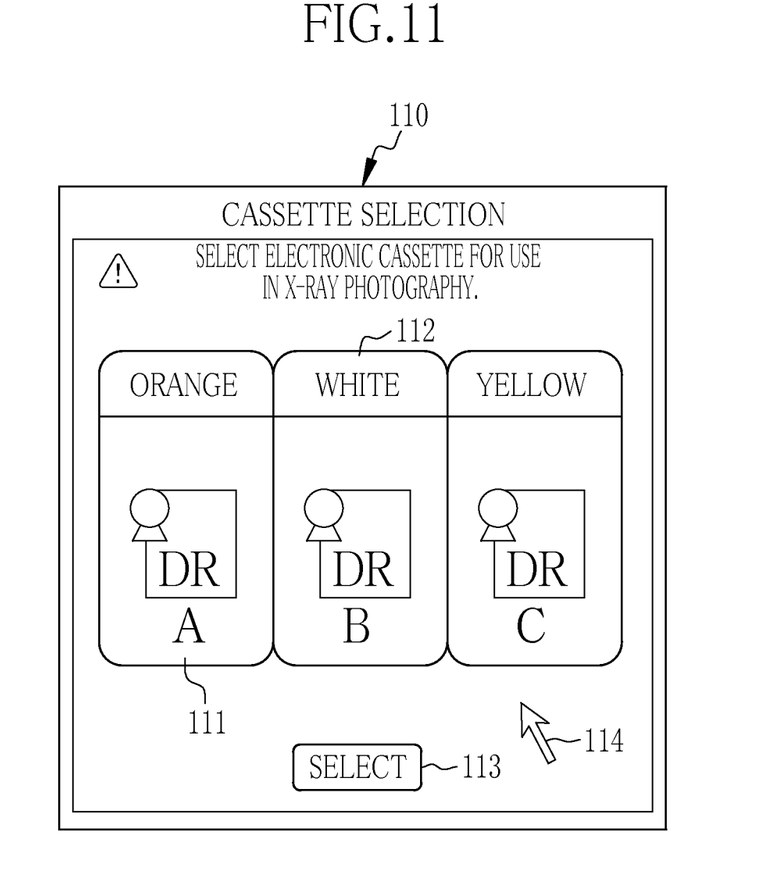
FIG. 11 is a view illustrating a cassette selection screen.

Prior to X-ray photography, an operator selects the electronic cassette 10 for use in the X-ray photography from among a plurality of the electronic cassettes 10A, 10B, . . . using the display screen and the input device of the control device 100. Simultaneously, a cassette selection screen 110 as shown in FIG. 11, for example, is displayed on the display screen. A selection button 111 and an emission color 112 for each of a plurality of the electronic cassettes 10A, 10B, . . . (e.g., electronic cassettes 10A, 10B, and 10C in FIG. 11) and a selection button 113 are displayed on the cassette selection screen 110. The operator selects the selection button 111 corresponding to the desired electronic cassette 10 using a cursor 114, and clicks the selection button 113. Thus, the selection of the electronic cassette 10 for use in the X-ray photography is completed.

The control device 100 transmits a selection designation signal indicating that the electronic cassette 10 has been selected to the electronic cassette 10 selected by the operator through the cassette selection screen 110. Upon receiving the selection designation signal, the electronic cassette 10 activates the light source 56 with use of the emission color registered as the emission color representing the selected state in the operation condition-emission color list 102.

Since the light source 56 is configured to emit the light L having the emission color preliminarily registered from among a plurality of emission colors in the selected state as described above, it is possible for the operator to readily tell whether or not the electronic cassette 10 which displays the selected state by the indicator 41 is identical with the electronic cassette 10 actually required to be used by the operator. Therefore, it is possible to prevent misidentification of the electronic cassettes 10.

Note that, in the case where a light-emitting element such as an LED contained in a case having a cannonball shape provided with a microlens is used as the light source 56, for example, the display window 57 consists of only the opening 59, and a front edge of the case is exposed through the opening 59, such that the opening 59 is blocked by the case instead of the cover 60. Alternatively, instead of using the front edge of the case, the entire light source 56 may be used to block the opening 59. In this case, the light source 56 is disposed not inside the housing 16 but outside the housing 16.

In order to distinguish the operation conditions of the electronic cassette 10 or distinguish the selected state of the electronic cassette 10 actually required to be used from among a plurality of the electronic cassettes 10, not only the color of the light L but also a lighting pattern of the light source 56 may be changed as follows. The light L may blink in red in the error state. The light L may blink in green in the case where the electronic cassette 10A is selected, and the light L may be continuously illuminated in green in the case where the electronic cassette 10B is selected.

The side panel of the outer grid is not necessarily provided for all the side surfaces 22 to 25. For example, an outer grid provided with a side panel only at a position facing the side surfaces 22 and 23 may be used. Further, each of the inclined surfaces 55 and 62 is not limited to the curved surface which is convex toward the outside of the housing 16 as described in the above embodiments, and may be a flat surface or may be in a shape obtained by combining a curved surface and a flat surface.

Note that, without using the scintillator, a direct conversion-type image detector using a conversion layer (amorphous selenium or the like) which directly converts the X-ray into the charge may be used. Furthermore, although the image detector of the TFT type is exemplified in the above embodiments, the present invention may adopt an image detector of a CMOS (Complementary Metal Oxide Semiconductor) type. Further, the present invention is also applicable to an electronic cassette and an electronic cassette system using other radiation rays such as γ-rays instead of the X-rays in radiography.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An electronic cassette system comprising:
  (A) an electronic cassette including:
    an image detector for detecting a radiation image of a subject based on radiation having been transmitted through the subject;
    a housing for housing the image detector, the housing having a front surface on which the radiation is incident, a rear surface facing the front surface, and four side surfaces, and the housing having an inclined surface which is formed at least between one of the side surfaces and the rear surface and inclined relative to the one of side surfaces and the rear surface; and
    an indicator having a light source and a display window disposed at least on the inclined surface such that light is emitted from the light source to the outside through the display window;
  (B) an outer grid detachably attached to the electronic cassette, for removing scattered rays generated upon transmission of the radiation through the subject; and
  (C) an installation surface on which the electronic cassette is installed, the installation surface reflecting the light from the display window,
  wherein the indicator represents operation conditions, and
  wherein the operation conditions include a selected state indicating that selection of an electronic cassette to be used in radiography has been completed.

2. The electronic cassette system according to claim 1, wherein
  the image detector has a rectangular imaging area, and
  the indicator is disposed at a center position of one side of the imaging area.

3. The electronic cassette system according to claim 1, wherein the display window is formed to extend from the inclined surface to the side surface.

4. The electronic cassette system according to claim 1, wherein the operation conditions further include at least one of a ready state indicating that preparation for detecting the radiation image by the image detector has been completed, and an error state indicating an abnormal operation.

5. The electronic cassette system according to claim 1, wherein the display window consists of an opening and a cover having light permeability, the cover blocking the opening.

6. The electronic cassette system according to claim 1, wherein the outer grid including:
  a top panel for covering the front surface of the housing; and
  a side panel provided to an edge of the top panel, the side panel extending in a direction from the front surface to the rear surface of the housing, so as to cover part of the side surface of the housing.

7. The electronic cassette system according to claim 2, wherein the display window has an elongated shape in which a longitudinal direction of the display window extends in a direction perpendicular to the one side of the imaging area.

8. The electronic cassette system according to claim 2, wherein a mark is formed on the side surface of the housing, the mark extending in a direction perpendicular to the one side of the imaging area from one end of the display window.

9. The electronic cassette system according to claim 8, wherein the mark is formed to extend from the side surface to the front surface of the housing.

10. The electronic cassette system according to claim 3, wherein the display window is formed to further extend from the side surface to the front surface.

11. The electronic cassette system according to claim 4, wherein the light source is configured to emit light having plural different colors and emit light having a color preliminarily registered from among the plural colors in the selected state.

12. An electronic cassette system comprising:
  (A) at least first and second electronic cassettes, each of the electronic cassettes including:
    an image detector for detecting a radiation image of a subject based on radiation having been transmitted through the subject;
    a housing for housing the image detector, the housing having a front surface on which the radiation is incident, a rear surface facing the front surface, and four side surfaces, and the housing having an inclined surface which is formed at least between one of the side surfaces and the rear surface and inclined relative to the one of the side surfaces and the rear surface;
    an indicator having a light source and a display window disposed at least on the inclined surface such that light is emitted from the light source to the outside through the display window; and
  (B) an outer grid detachably attached to one of the electronic cassettes, for removing scattered rays generated upon transmission of the radiation through the subject; and
  (C) an installation surface on which the first and second electronic cassettes are installed, the installation surface reflecting the light from the display windows,
  wherein each of the indicators represents operation conditions that include a selected state indicating that one of the electronic cassettes has been selected for use in radiography, and
  wherein the light source of the first electronic cassette and the light source of the second electronic cassette emit light having different colors in the selected state.

13. The electronic cassette system according to claim 12, further comprising:
  (D) a control device having a display screen on which colors of the light to be emitted from the electronic cassettes in the selected states are displayed.

* * * * *